United States Patent [19]

Kloss et al.

[11] Patent Number: 4,937,355

[45] Date of Patent: Jun. 26, 1990

[54] PROCESS FOR PREPARING (TRANS)-4-SUBSTITUTED-DL-PROLINE DERIVATIVES

[75] Inventors: John Kloss, Holland; David Kronenthal, Yardley, both of Pa.; Christopher M. Cimarusti, Somerset; Richard H. Mueller, Ringoes, both of N.J.

[73] Assignee: E. R. Squibb & Sons, Inc., Princeton, N.J.

[21] Appl. No.: 297,522

[22] Filed: Jan. 17, 1989

[51] Int. Cl.$^5$ .................. C07D 207/08; C07D 207/46
[52] U.S. Cl. ..................................... 548/532; 548/533; 548/535
[58] Field of Search .............. 548/532, 535, 533, 536, 548/539, 540, 542

[56] References Cited

U.S. PATENT DOCUMENTS

| | | | |
|---|---|---|---|
| 4,316,905 | 2/1982 | Krapcho | 514/423 |
| 4,337,201 | 6/1982 | Petrillo, Jr. | 548/413 |
| 4,462,943 | 7/1984 | Petrillo, Jr. et al. | 514/19 |
| 4,501,901 | 2/1985 | Thottathil et al. | 548/532 |
| 4,588,819 | 5/1986 | Thottatil | 548/532 |

FOREIGN PATENT DOCUMENTS

0201349 11/1986 European Pat. Off. .
2585354 1/1987 France .

OTHER PUBLICATIONS

Ihara et al., J. Chem. Soc. Perkin Trans I (1986), pp. 1543–1549.
Shiozaki et al., Heterocycles, vol. 22, No. 8 (1984), pp. 1725–1726.
J. Med. Chem (88) 31/6, 1148–60.
Helvetica Chimica Acta, vol. 64, Fasc. 7 (1981), Nr. 215, pp. 2203–2218.
Tetrahedron Letter, vol. 27, No. 47, pp. 5707–5710 (1986).

Primary Examiner—Joseph Paul Brust
Assistant Examiner—MarySue Howard
Attorney, Agent, or Firm—Burton Rodney

[57] ABSTRACT

A process is provided for preparing (trans)-4-phenyl-DL-proline derivatives, which are useful in preparing certain angiotensin converting enzyme inhibitors, which process involves reacting an ester of the structure

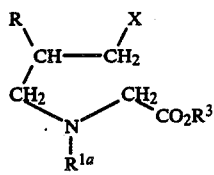

wherein X is a leaving group such as tosylate, $R^3$ is lower alkyl, R is cyclohexyl, phenyl or substituted phenyl, and $R^{1a}$ is a protecting group, with a potassium amide base such as potassium hexamethyldisilazide under reduced temperatures to form the trans-4-substituted proline ester derivative of the structure

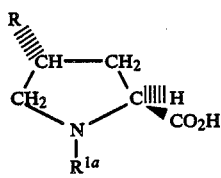

then hydrolyzing the proline ester to the acid of the structure

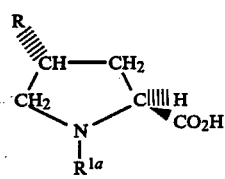

and removing the $R^{1a}$ nitrogen protecting group to form the unprotected acid of the structure

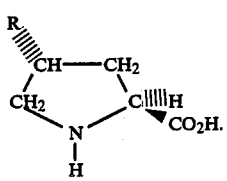

6 Claims, No Drawings

PROCESS FOR PREPARING (TRANS)-4-SUBSTITUTED-DL-PROLINE DERIVATIVES

FIELD OF THE INVENTION

The present invention relates to a process for preparing trans-4-substituted-DL-proline derivatives with excellent stereospecificity, whose derivatives are intermediates in the preparation of certain angiotensin-converting enzyme inhibitors.

DESCRIPTION OF THE INVENTION

In accordance with the present invention, a process is provided for preparing (trans)-4-substituted-DL-proline derivatives of the structure I

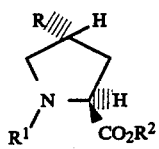

wherein R is phenyl, cyclohexyl, or phenyl substituted with halogen such as F, Cl or Br in o or p positions or mixtures, $R^1$ is hydrogen or a nitrogen protecting group (such as acetyl, benzoyl, p-anisoyl, p-nitrobenzoyl, trifluoroacetyl, o-toluoyl, p-toluoyl, p-tosyl, p-chlorobenzoyl, o-chlorobenzoyl, carbobenzyloxy, t-butoxycarbonyl, methoxycarbonyl, phenyloxycarbonyl, t-butylcarbonyl, and the like), and $R^2$ is H, aryl or lower alkyl, which process involves a highly trans stereoselective intramolecular alkylation (ring closure). The process of the invention includes the steps of reacting an ester of the structure II

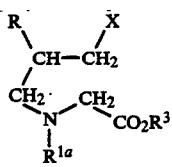

wherein X is a leaving group which is a halide such as chloride, a $C_1$ to $C_6$ alkyl sulfonate such as mesylate or triflate, or aryl sulfonate such as tosylate, or a cycloalkylsulfonate such as cyclohexylsulfonate; $R^3$ is lower alkyl; R is as defined above; and $R^{1a}$ is a nitrogen protecting group as defined above for $R^1$; with a potassium amide base such as potassium hexamethyldisilazide, in the presence of an inert organic solvent such as tetrahydrofuran, diethyl ether, or toluene under reduced temperatures, to facilitate ring closure and form the trans-4-substituted-DL-proline ester derivative III.

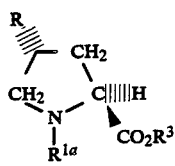

The ester III may then be hydrolyzed to the corresponding acid IV by treating ester III with a base such as an alkali metal hydroxide, such as lithium hydroxide, sodium hydroxide or potassium hydroxide, to form the corresponding alkali metal salt, and treating the salt with strong mineral acid, such as HCl, to form the acid IV.

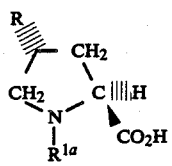

The nitrogen protecting group $R^{1a}$ may be removed by suitable art recognized methods. For example where $R^{1a}$ is carbobenzyloxy, $R^{1a}$ may be removed by hydrogenating acid IV in the presence of a hydrogenation catalyst such as palladium on charcoal or palladium hydroxide on carbon (Pearlman's catalyst) in an alcohol solvent, such as methanol, to form acid V.

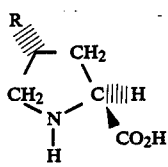

Amide protecting groups $R^{1a}$ may be removed by hydrolysis with strong acid, i.e. 6N HCl, 100° C.; t-butoxycarbonyl may be removed by acid under milder conditions (trifluoroacetic acid, room temperature or HCl, room temperature).

The process of the invention will produce the predominantly trans-4-substituted -DL-proline derivative I and a small amount of the corresponding cis derivative, so that the ratio of trans:cis in the product will be at least about 90:10 or more and preferably at least about 95:5 or more and more preferably about 97:3.

In carrying out the process of the invention, the ester derivative II will be employed in a molar ratio to the potassium amide base of within the range of from about 1:1 to about 1:1.2 and preferably from about 1:1 to about 1:1.05. The reaction will be carried out at a reduced temperature of within the range of from about −40° C. to about −90° C. and preferably from about −60° C. to about −80° C.

The starting ester II may be prepared by reacting ester VI

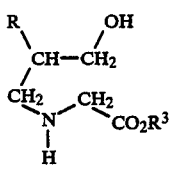

with a protecting compound VII or VIIA $R^{1a}Cl$ or     VII $(R^{1a})_2O$     VIIA wherein $R^{1a}$ represents a nitrogen protecting group as set out above for $R^1$, to form the protected ester VIII

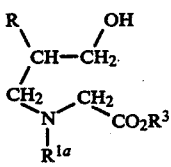

VIII

Protected ester VIII is then treated to replace the OH group with a leaving group by reacting VIII with a $C_1$ to $C_6$ alkyl sulfonate chloride, such as tosyl chloride or mesyl chloride, or cyclohexylsulfonyl chloride, in the presence of dimethylaminopyridine (DMAP) and Hünig's base (diisopropylethylamine), and in inert solvent such as methylene chloride to form the ester II

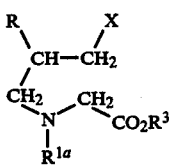

II

Ester VI may be prepared by treating a solution of a diethylmalonate A.

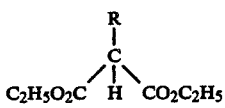

A.

with borane-methyl sulfide complex, in an aromatic solvent such as toluene to form the corresponding 1,3-propanediol B.

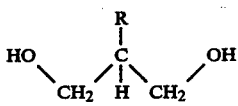

B.

which is treated with base such as sodium hydride in the presence of an inert solvent such as tetrahydrofuran under an inert atmosphere such as argon. Acetyl chloride is then added to form the corresponding acetate ester C.

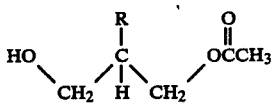

C.

Compound C is in the form of a racemic mixture (DL). However, chiral C, may be obtained by the enzymatic hydrolysis of diacetate $C^1$ (prepared by treating B. with excess acetic anhydride or acetyl chloride)

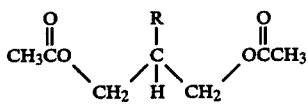

$C^1$.

(as described by G. M. Ramos Tombo et al., Tetrahedron Letters, Vol. 27, No. 47, Pages 5707–5710 (1986). By using optically active C. and carrying out the steps as described below, the L-series of proline derivatives may be prepared.

A solution of the ester C. and triphenyl phosphine in dichloromethane is stirred under an inert atmosphere such as argon and treated with phthalimide. The mixture is cooled to less than 25° C. and treated with diisopropylazodicarboxylate in dichloromethane to form the imide acetate D.

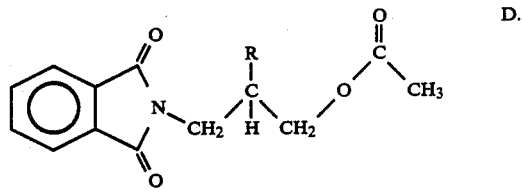

D.

A solution of imide D. in methanol is treated with potassium carbonate to afford the imide alcohol E.

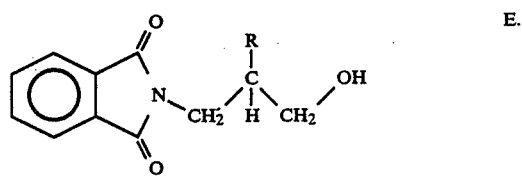

E.

Treatment of compound E. with methylhydrazine in methanol initially at room temperature and then at reflux produces the amine F.

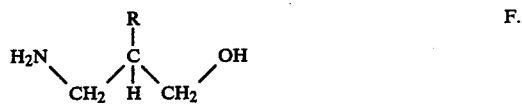

F.

A solution of amine F. and methyl glyoxylate methylhemiacetal in methanol is stirred initially under an inert atmosphere such as argon and then hydrogenated to form ester VI.

Additionally compound VI can also be prepared by reacting the dialdehyde G.

G.

with N-benzylglycine ester H. in ethyl alcohol or acetic acid to produce the adduct J.

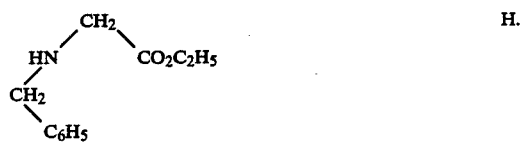

H.

J.

which is hydrogenated to produce adduct VI where $R^3$ is $C_2H_5$.

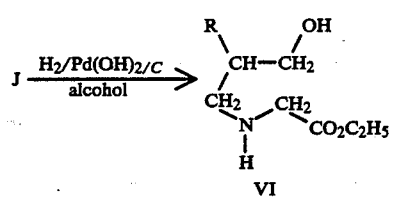

Examples of starting ester compounds II useful in carrying out the process of the invention include, but are not limited to, the following.

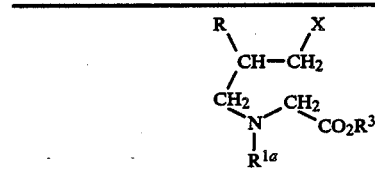

| X | R¹ᵃ | R³ | R |
|---|---|---|---|
| tosylate | C₆H₅C(O)— | CH₃ | 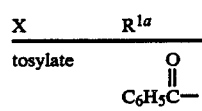 |
| cyclohexyl-sulfonate | C₆H₅C(O)— | C₂H₅ | 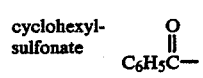 |
| tosylate | C₆H₅OC(O)— | CH₃ | 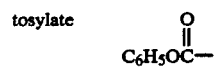 |
| tosylate | C₆H₅OC(O)— | CH₃ | 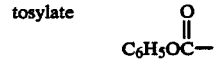 |
| tosylate | C₆H₅C(O)— | CH₃ | 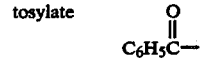 |
| mesylate | C₆H₅C(O)— | CH₃ | 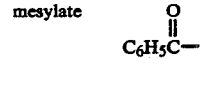 |
| triflate | CH₃SO₂— | CH₃ | 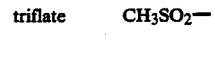 |
| triflate | C₆H₅C(O)— | CH₃ | 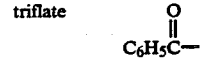 |
| tosylate | p-NO₂—C₆H₄— | C₂H₅ | 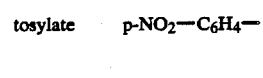 |

-continued

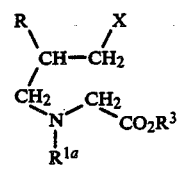

| X | R¹ᵃ | R³ | R |
|---|---|---|---|
| tosylate | CH₃C(O)— | C₂H₅ | 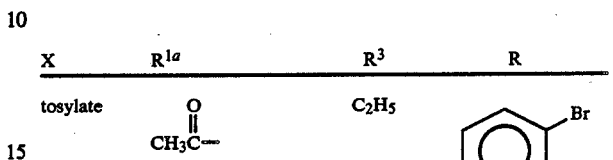 |
| tosylate | CF₃—C(O)— | C₂H₅ |  |
| mesylate | C₆H₅C(O)— | CH₃ |  |
| mesylate | o-Cl—C₆H₄C(O)— | CH₃ |  |
| tosylate | C₆H₅C(O)— | CH₃ |  |
| mesylate | p-tosyl | n-C₃H₇ | 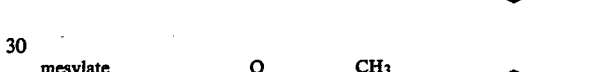 |
| cyclohexyl-sulfonate | o-Cl—C₆H₄C(O)— | n-C₄H₉ |  |
| tosylate | o-Cl—C₆H₄C(O)— | CH₃ |  |

The trans-4-substituted-L-proline derivatives (prepared by using optically active C. in place of the racemic mixture of C. as described above) may be employed to form angiotensin converting enzyme inhibitors as described in U.S. Pat. No. 4,337,201 to Petrillo which covers fosinopril which has the following formula:

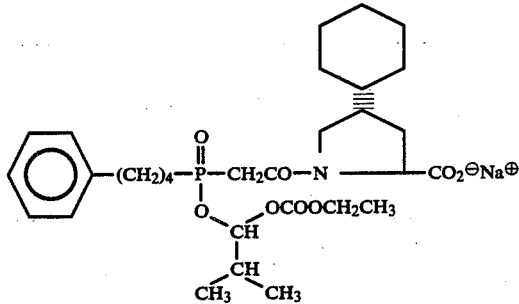

Listed below are definitions of the terms used in this specification. These definitions apply to the terms as they are used throughout the specification (unless they are otherwise limited in specific instances), either individually or as part of a larger group.

The terms "alkyl" and "alkoxy" refer to both straight and branched chain groups. Those groups having 1 to 10 carbon atoms are preferred.

The terms "cycloalkyl" and "cycloalkenyl" refer to groups having 3 to 7 carbon atoms.

The term "aryl" refers to phenyl or phenyl substituted with halogen, alkyl, alkoxy, alkylthio, hydroxy, alkanoyl, nitro, amino, dialkylamino, or trifluoromethyl groups.

The term "alkanoyl" refers to groups having 2 to 9 carbon atoms.

The term "halogen" refers to fluorine, chlorine, bromine and iodine.

The following Examples represent preferred embodiments of the present invention. All temperatures are expressed in degrees Centigrade.

EXAMPLE 1 trans-4-Cyclohexyl-N-carbobenzyloxy-DL-proline, methyl ester

A. Diethyl cyclohexylmalonate

A suspension of 5% rhodium on carbon (4.5 g) and diethyl phenylmalonate (30 g) in ethanol (100 ml) was hydrogenated at 60 psi for 18 hours. The suspension was filtered through celite and concentrated to a syrup (quant. yield). Distillation at 90°–94° C. (0.5 mmHg) afforded 28.2 g (92%) of the diethyl cyclohexylmalonate.

B. 2-Cyclohexyl-1,3-propanediol

Borane-methyl sulfide complex (approximately 10M in $BH_3$, 62 ml, 0.62 mol) was added dropwise to a solution of diethyl cyclohexylmalonate (58.6 g, 0.242 mol) in toluene (100 ml). The solution was heated to 45° C. then the external heating removed. After the reaction exotherm had subsided, it was heated to 90° C. and maintained there for 3 days. At this temperature, the liberated dimethyl sulfide slowly distilled and was collected.

After cooling to room temperature, the excess borane was destroyed by the careful dropwise addition of methanol (20 ml). An additional portion of methanol (30 ml) containing a catalytic amount of sulfuric acid was added and the methanol distilled. Portionwise additions of methanol (10×250 ml) were added and distilled. When the distillate tested free of boron (green boron flame test), the residue was concentrated on a rotary evaporator to remove the residual methanol. Dichloromethane (250 ml) was added and the hazy solution filtered through celite. The celite was washed with warm dichloromethane and the combined filtrates concentrated to a solid. Toluene (100 ml) was added and the solids filtered then dried in vacuo to afford 2-cyclohexyl-1,3-propanediol (34.5 g, 90%).

C. 2-Cyclohexyl-1,3-propanediol, monoacetate ester

Sodium hydride (60% in oil, 111 mg, 2.78 mmol) was added to a solution of 2-cyclohexyl-1,3-propanediol (350 mg, 2.22 mmol) in tetrahydrofuran (15 ml), and the suspension stirred under argon for 1 hour. Acetyl chloride (200 ml, 2.79 mmol) was added at −10° and the mixture stirred for 18 hours at room temperature. After quenching with acetic acid, hexanes (15 ml) was added and the mixture extracted with dilute HCl (once), water (three times), and saturated NaCl (once). The organic phase was dried ($MgSO_4$), filtered, concentrated to a syrup, and applied to a silica gel column. Elution with hexane-diethyl ether (2:1 then 3:5) and concentration of the appropriate fractions afforded 355 mg (80%) of 2-cyclohexyl-1,3-propanediol, monoacetate ester.

D. 3-Amino-2-cyclohexyl-1-propanol

A solution of 2-cyclohexyl-1,3-propanediol, monoacetate ester (15 g, 75 mmole) and triphenylphosphine (22.86 g, 87.15 mmole) in dichloromethane (200 ml) was stirred under argon and treated with phthalimide (12.14 g, 82.5 mmole). The resulting mixture (heterogeneous) was cooled to 20° C. and treated dropwise over 50 minutes with a solution of diisopropylazodicarboxylate (16.5 ml, 84 mmole) in dichloromethane (50 ml). A cooling bath was used to maintain an internal temperature of 20°–25° C. during the addition. The reaction was then stirred at ambient temperature for 4 hours. The solvent was evaporated and methanol (100 ml) was added and evaporated (repeat one additional time). The residue was dissolved in methanol (300 ml), treated with potassium carbonate (3 g, 22.5 mmole) and stirred under argon at ambient temperature overnight.

The solvent was removed in vacuo and the residue was treated with dichloromethane and filtered. The filtrate was washed with water and brine and dried. Filtration followed by concentration in vacuo produced an oil which was dissolved in methanol (250 ml) and treated dropwise over 5 minutes with methylhydrazine (12 ml, 225 mmole). The reaction was stirred under argon at ambient temperature overnight, and then refluxed for 4 hours.

The reaction was cooled to room temperature, stirred overnight and concentrated in vacuo. The residue was treated with toluene (200 ml) which was then evaporated to remove traces of methylhydrazine (repeat twice with toluene and once with methanol).

The residue was dissolved in methanol and treated with a solution of concentrated hydrochloric acid (8 ml) in methanol (30 ml). The mixture was stirred at room temperature for 2 hours and filtered to remove N-methylphthalhydrazide. The filtrate was concentrated and methanol was added to the residue. The resulting slurry was filtered to remove additional N-methyl phthalhydrazide.

The filtrate was concentrated in vacuo and partitioned between water (300 ml) and dichloromethane (300 ml). The aqueous layer was washed with additional dichloromethane (5 times 100 ml) and the pH was raised to 9 with sodium hydroxide. The volume was concentrated in vacuo by ca. 30%, toluene (150 ml) was added and the biphasic mixture was cooled to 0° C. While vigorously stirring, the pH of the aqueous layer was raised to 11.3 with sodium hydroxide. The layers were separated and the aqueous layer was saturated with sodium chloride and washed with additional toluene. The organic extracts were dried and concentrated in vacuo to a blue-green liquid which was dissolved in methanol (60 ml) and treated with 1 g of activated charcoal. After stirring for 30 minutes, filtration followed by concentration in vacuo afforded 7.56 g (64%) of the title compound.

E. N-(2-Cyclohexyl-3-hydroxypropyl) glycine, methyl ester

A solution of 3-amino-2-cyclohexyl-1-propanol (1 g, 6.37 mmole) and methyl glyoxylate methylhemiacetal (790 mg, 6.56 mmole; see Tetrahedron, 881, 1977) in methanol (9 ml) was stirred at room temperature under argon for 24 hours. The resulting solution was transferred to a Parr bottle, treated with additional methanol (22 ml), acetic acid (3.6 ml), and 10% Pd on carbon (857 mg) and hydrogenated at 50 psi overnight. The catalyst was filtered off and the filtrate was concentrated in vacuo. Acetic acid was removed by evaporation from toluene. The residue was partitioned between ethyl acetate and 1N HCl. The organic layer was extracted with additional HCl and the combined aqueous extracts were washed with ethyl acetate. The pH of the product rich aqueous solution was raised to 10.2, and sodium chloride was added to saturation. Extraction with ethyl acetate followed by drying (sodium sulfate), filtration and concentration in vacuo produced 780 mg (53%) of the title compound as an oil.

F. N-(2-Cyclohexyl-3-hydroxypropyl)-N-[(phenylmethoxy)carbonyl]glycine, methyl ester Potassium carbonate (5.6 g) was added to a mixture of the crude Part E cyclohexyl derivative (15.2 g) in tetrahydrofuran-water (1:1, 300 ml) at 0° C. The rapidly stirred mixture was adjusted to pH 8 with additional $K_2CO_3$. Carbobenzyloxy chloride (8 ml) and $K_2CO_3$ were added to maintain the pH between 8-8.5. After stirring for an additional 30 minutes at 0° C., solid NaCl was added. The mixture was then extracted with ethyl acetate. The extract was diluted with diethyl ether-hexanes (1:1, 200 ml) and the solution extracted with dilute HCl (once), saturated $NaHCO_3$ (once), saturated NaCl (twice), and saturated NaCl (once). The organic phase was dried ($MgSO_4$), filtered, concentrated to a syrup and chromatographed over silica gel. Elution with hexane-diethyl ether (3:1 to 1:1) yielded 5.5 g of the title carbobenzyloxy-protected glycine derivative.

G. N-[2-Cyclohexyl-3-[[(4-methylphenyl)sulfonyl]oxy]propyl]-N-[(phenylmethoxy)carbonyl]glycine, methyl ester Tosyl chloride (3.41 g, 17.9 mmol) and N,N-dimethylaminopyridine (DMAP) (1.99 g, 1.63 mmol) were added to a solution of Part F ester (6.1 g, 16.3 mmol) and diisopropylethylamine (3.7 ml, 21.2 mmol) in $CH_2Cl_2$ (100 ml). After 4 hours, the solution was diluted with ethyl acetate (300 ml) and the mixture extracted with dilute HCl (twice), water (once), dilute $NaHCO_3$ (twice), water (once), and saturated NaCl (twice). The organic phase was dried ($MgSO_4$), filtered, concentrated to a syrup, and applied to a silica gel column. Elution with hexanes-diethyl ether (2:1 then 1:1) yielded 7.17 g (85%, 2 steps) of the title tosylate.

H. trans-4-Cyclohexyl-N-carbobenzyloxy-DL-proline, methyl ester

Potassium hexamethyldisilazide (0.533M in toluene, 9.1 ml) was added dropwise to a solution of the Part G tosylate (2.51 g, 4.86 mmol) in tetrahydrofuran (90 ml) at −78° C. The yellow solution was stirred at −78° C. for 2 hours before being quenched by the dropwise addition of acetic acid (0.5 ml). The mixture was stirred for 5 minutes then allowed to warm to approximately −50° C. before the addition of hexanes (120 ml). The mixture was extracted with dilute HCl (once), water (once), saturated $NaHCO_3$ (twice), water (once) and saturated NaCl (once). The organic phase was dried ($MgSO_4$), filtered, and concentrated to a syrup. A 270 MHz NMR spectrum of the crude product showed it to be a 989:2 mixture of trans:cis prolines, 1.33 g (80%).

EXAMPLE 2 trans-4-Cyclohexyl-N-carbobenzyloxy-DL-proline

A solution of $LiOH·H_2O$ (342 mg, 8.16 mmol) in $H_2O$ (18 ml) was added to a solution of the Example 1 proline methyl ester (1.34 g, 3.88 mmol) and $H_2O$ (4 ml) in tetrahydrofuran (25 ml). After 2 hours, a TLC of the biphasic cloudy reaction mixture showed very little hydrolysis. Small amounts of $H_2O$ and tetrahydrofuran were added in order to make a monophasic clear solution. After an additional 2 hours, hydrolysis was complete. The reaction was adjusted to pH 8 and extracted with ethyl acetate (three times). The aqueous phase was adjusted to pH 2 and extracted with ether (three times). The combined ether extracts were dried ($MgSO_4$), filtered, and concentrated to 1.04 g (86%) of title compound as a colorless syrup.

EXAMPLE 3 trans-4-Cyclohexyl-DL-proline

A solution of the Example 2 proline (1.04 g, 3.14 mmole) in methanol was treated with 10% Pd/C (125 mg) and hydrogenated at atmospheric pressure for 2 hours. The mixture was heated on a steam bath and filtered through celite. The filtrate was concentrated to a solid, co-evaporated once with toluene, and then vacuum dried overnight to give 587 mg (90%) of title compound. An HPLC analysis of the product showed a 97:3 (trans:cis) mixture of prolines.

EXAMPLES 4 TO 14

Following the procedure of Example 1 except substituting the ester shown in Column I below for the ester used in Example 1, and substituting, where necessary, the protecting compound shown in Column II for the carbobenzyloxy chloride, the following products were obtained as shown in Column III.

| I<br>Starting Ester | II<br>Protecting<br>Compound | III<br>Products |
| --- | --- | --- |

-continued

| | R−CH−CH₂ with OH, CH₂−N(H)−CH₂−CO₂R³ | | | R¹ᵃCl | | | R (pyrrolidine) with CO₂R³, N−R¹ᵃ | | Ratio (trans:cis) | |
|---|---|---|---|---|---|---|---|---|---|---|
| Ex. No. | R | R³ | R¹ᵃ | | R | R³ | R¹ᵃ | | NMR | HPLC |
| 4. | phenyl | CH₃ | COC(CH₃)₃ | | | | | | 94:6 | |
| 5. | phenyl | C₂H₅ | COCH₂C₆H₅ | | as in Column I | | as in Column II | | >85:15 | |
| 6. | phenyl | CH₃ | COCH₂C₆H₅ | | | | | | 95:5 | 93:7 |
| 7. | cyclohexyl | C₂H₅ | COC(CH₃)₃ | | | | | | 98:2 | |
| 8. | cyclohexyl | CH₃ | COC(CH₃)₃ | | | | | | >98:2 | |
| 9. | cyclohexyl | C₂H₅ | COCH₂C₆H₅ | | | | | | 98:2 | |
| 10. | cyclohexyl | CH₃ | COCH₂C₆H₅ | | as in Column I | | as in Column II | | 98:2 | 97:3 |
| 11. | cyclohexyl | C₂H₅ | COCH₃ | | | | | | | |
| 12. | cyclohexyl | CH₃ | COC₆H₅ | | | | | | 98:2 | |
| 13. | cyclohexyl | CH₃ | CC(CH₃)₃ | | | | | | 98:2 | |
| 14. | cyclohexyl | CH₃ | CC₆H₅ | | | | | | 90:10 | |

| | | |
|---|---|---|
| 15. | 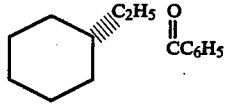 | 90:10 |

EXAMPLES 15 TO 25

Following the procedure of Example 2 except substituting the ester product of Examples 2 to 12 for the Example 1 compound, the corresponding protected acids are obtained.

EXAMPLES 26 TO 36

The protected acids of Examples 15 to 25 may be deprotected using standard procedures.

What is claimed is:

1. A process for preparing trans-4-substituted protected proline derivatives of the structure

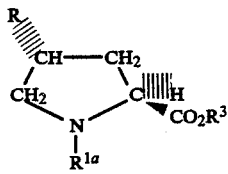

wherein
R is cyclohexyl, phenyl or phenyl substituted with halogen;
$R^{1a}$ is a nitrogen protecting group; and
$R^3$ is lower alkyl, which comprises reacting an ester of the structure

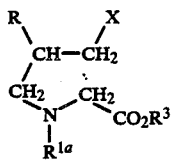

wherein R is as defined above, $R^{1a}$ is a nitrogen protecting group, $R^3$ is defined above and X is a leaving group which is a halide, a $C_1$ to $C_6$ alkyl sulfonate, aryl sulfonate or cycloalkylsulfonate, with a potassium amide base which is potassium hexamethyldisilazide to facilitate ring closure and form the trans-4-substituted-N-protected proline ester of the structure

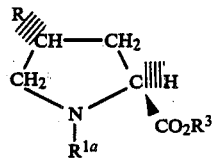

2. The process as defined in claim 1 wherein reaction of the ester with the potassium amide base is carried out at a temperature within the range of from about $-40°$ C. to about $-90°$ C. employing a molar ratio of ester:potassium amide base of within the range of from about 1:1 to about 1:1.2.

3. The process as defined in claim 1 wherein the nitrogen protecting group is acetyl, benzoyl, p-anisoyl, p-nitrobenzoyl, trifluoroacetyl, o-toluoyl, p-toluoyl, p-tosyl, p-chlorobenzoyl, o-chlorobenzoyl, carbobenzyloxy, t-butoxycarbonyl, methoxycarbonyl, phenyloxycarbonyl or t-butylcarbonyl.

4. The process as defined in claim 1 wherein the X leaving group is a $C_1$ to $C_6$ alkyl sulfonate, aryl sulfonate or cycloalkylsulfonate.

5. The process as defined in claim 4 wherein the X leaving group is tosylate, mesylate, triflate, halide or cyclohexylsulfonate.

6. The process as defined in claim 1 wherein the ester starting material has the structure

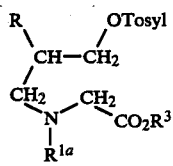

wherein R is phenyl or cycloalkyl, $R^{1a}$ is

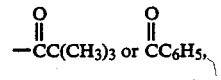

and $R^3$ is $CH_3$ or $C_2H_5$.

* * * * *